(12) United States Patent
Olsson

(10) Patent No.: US 6,178,347 B1
(45) Date of Patent: Jan. 23, 2001

(54) APPARATUS FOR FREQUENCY ANALYSIS OF ATRIAL FIBRILLATION

(76) Inventor: Bertil Olsson, SE-237 34, Bjärred (SE)

( * ) Notice: Under 35 U.S.C. 154(b), the term of this patent shall be extended for 0 days.

(21) Appl. No.: 09/180,238

(22) PCT Filed: Jun. 2, 1997

(86) PCT No.: PCT/SE97/00950

§ 371 Date: Jan. 8, 1999

§ 102(e) Date: Jan. 8, 1999

(87) PCT Pub. No.: WO97/48336

PCT Pub. Date: Dec. 24, 1997

(30) Foreign Application Priority Data

Jun. 18, 1996 (SE) .................................................... 9602394

(51) Int. Cl.$^7$ .................................................. A61B 5/046
(52) U.S. Cl. .......................................................... 600/518
(58) Field of Search ............................................... 600/518

(56) References Cited

U.S. PATENT DOCUMENTS

| 4,523,595 | 6/1985 | Zibell . | |
|---|---|---|---|
| 5,439,004 | 8/1995 | Duong-Van et al. . | |
| 5,772,604 | * 6/1998 | Langberg et al. | 600/518 |
| 5,843,133 | * 12/1998 | Routh et al. | 607/14 |
| 6,035,231 | * 3/2000 | Sörnmo et al. | 600/509 |

FOREIGN PATENT DOCUMENTS 2070871 9/1981 (GB) .

* cited by examiner

*Primary Examiner*—Carl H. Layno
(74) *Attorney, Agent, or Firm*—Ladas and Parry

(57) ABSTRACT

An apparatus for frequency analysis of atrial fibrillation, as a measure of the state of the illness which includes a device for registration of electrical signals from the heart of a patient, a device for separating a signal originating from the atrium and a device for frequency analysis of the atrial signal. Preferably, the separating device has a system for identification of signals originating from the ventricles, a system for classification of the ventricular signals, a system for formation of the average of the classified ventricular signals and a system for subtracting the averaged, classified ventricular signals from the total registered signal, in order to obtain the atrial signal. Preferably, the registration device comprises electrodes to be placed on the patient and for simultaneous registration of conventional ECG signals.

7 Claims, 8 Drawing Sheets

R  R  R  R

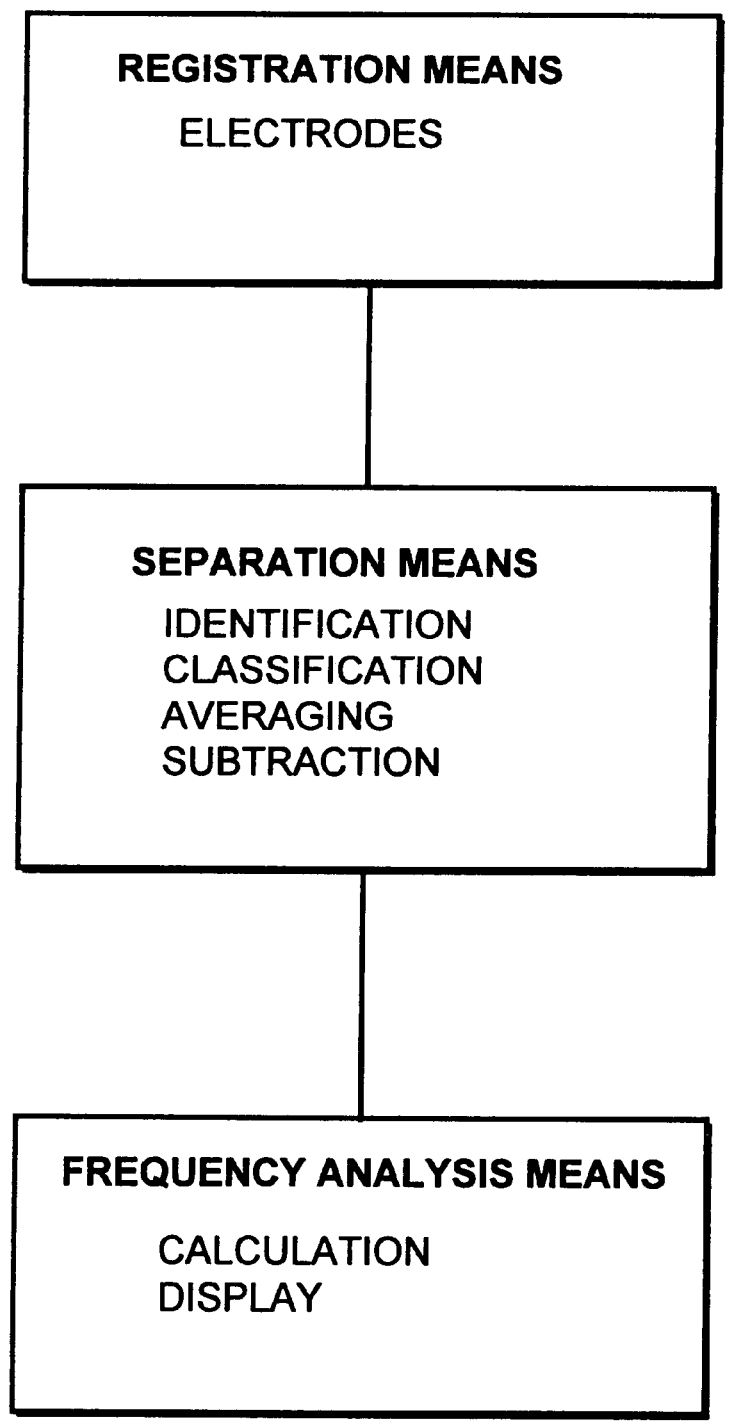
F I G. 7

APPARATUS FOR FREQUENCY ANALYSIS OF ATRIAL FIBRILLATION

FIELD OF THE INVENTION

The present invention relates to an apparatus for frequency analysis of atrial fibrillation, i.e. a means for determining a measure of the state of illness in connection with atrial fibrillation. The invention may be used to decide if and how the condition is to be treated.

The invention may be regarded as a further development of conventional ECG equipment. By means of the invention, the ECG signals can be processed in order to acquire information about the atrial fibrillation. This information will provide useful knowledge about the mechanism of the atrial fibrillation and the information will be used for assessing the state of illness of the patient.

STATE OF THE ART

The electrocardiogram technology (ECG) has been used for a long time to study the function of the heart. One disorder of the heart that may be determined by ECG is atrial fibrillation. To date, only superficial qualitative analyses of the atrial fibrillation have been performed, and it has not been possible to draw other clinically useful conclusions than if it is occurring or not.

With atrial fibrillation, the progression of the illness is sometimes such that it will reoccur spontaneously after a treatment. With the previously known technology it has not been possible to determine whether the treatment of the atrial fibrillation will be successful or how long time it will take before the fibrillation will reoccur spontaneously. Consequently, resources have sometimes been used unnecessarily for ineffective treatments.

The present invention eliminates, or at least reduces, this problem through the fact that the atrial fibrillation can be qualitatively analysed by studying its frequency behavior. With the aid of the invention, more accurate predictions can be made about whether a treatment of the atrial fibrillation will be successful or not.

SUMMARY OF THE INVENTION

The invention thus provides an apparatus for frequency analysis of atrial fibrillation. The apparatus comprises a means for registering electrical signals from the heart of a patient, a means for separating a signal originating from the atria and a means for frequency analysis of the atrial signal.

Preferably, the registration means comprises electrodes to be placed on the patient and for simultaneous registration of conventional ECG signals.

BRIEF DESCRIPTION OF THE DRAWINGS

The invention will be described in detail below, with reference to the accompanying drawings, of which:

FIG. 7 is a block diagram of apparatus for carrying out the invention.

DETAILED DESCRIPTION OF PREFERRED EMBODIMENTS

Investigations have shown that the illness of atrial fibrillation occurs with increasing frequency with increasing age. Below the age of 50 the illness is uncommon, but above that age it increases rather sharply. It is calculated that in Sweden there are about 100,000 people suffering from this illness in its chronic form.

Figure 1:
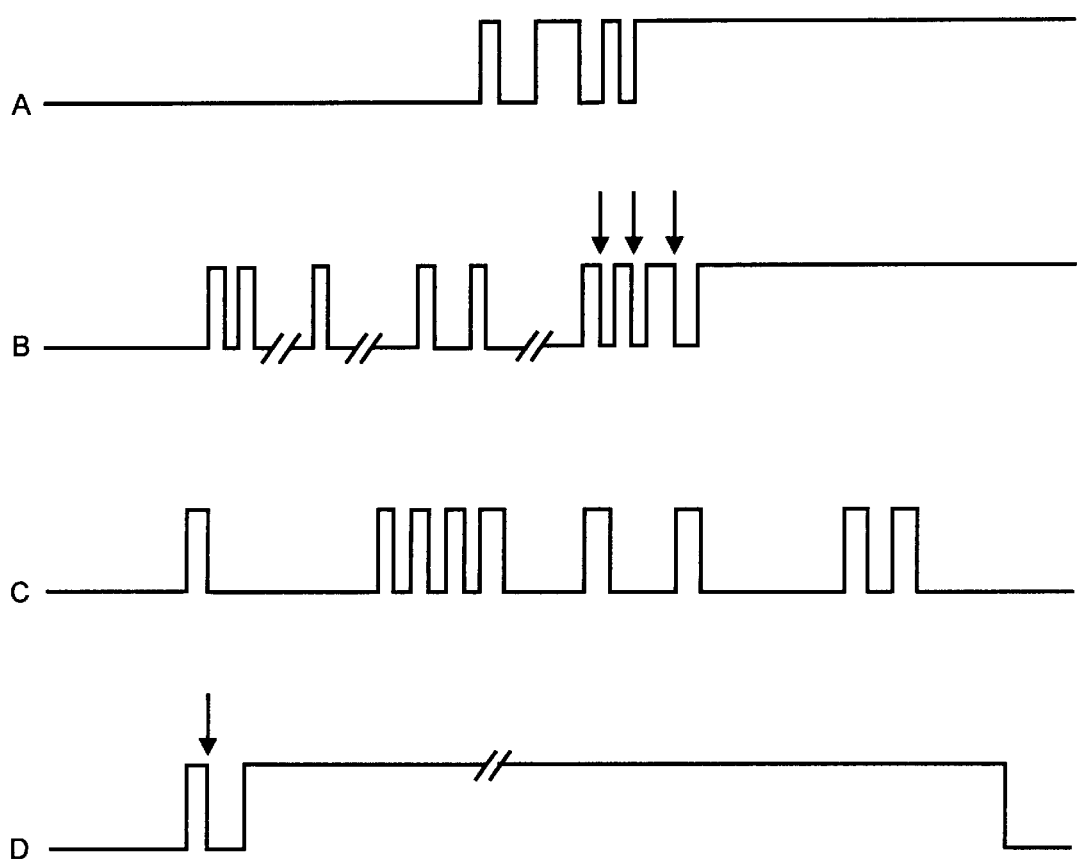
FIGS. 1A–D is a diagram showing known different courses of illness in connection with atrial fibrillation.

FIG. 1 shows some typical courses of illness for atrial fibrillation. In the diagram, a high level denotes the occurrence of atrial fibrillation and a low level denotes no occurrence. The vertical arrows show where treatment has been applied. As shown in curve A, the treatments are temporarily successful, but the illness reoccurs, each time after a shorter period of time. Finally, it is not worthwhile to perform any treatment. In the case of B, the illness subsides spontaneously a few times before taking the same course as in A, i.e. finally reaching a state of chronic atrial fibrillation. In the case of C, the illness occurs from time to time but never develops into chronic atrial fibrillation. In the case of D, the illness prevails during a prolonged period of time but withdraws spontaneously, without treatment. There are thus several varieties in existence and there is a need for an apparatus and a method for evaluating the atrial fibrillation in order to determine if a treatment has a chance of being successful.

Figure 2A:
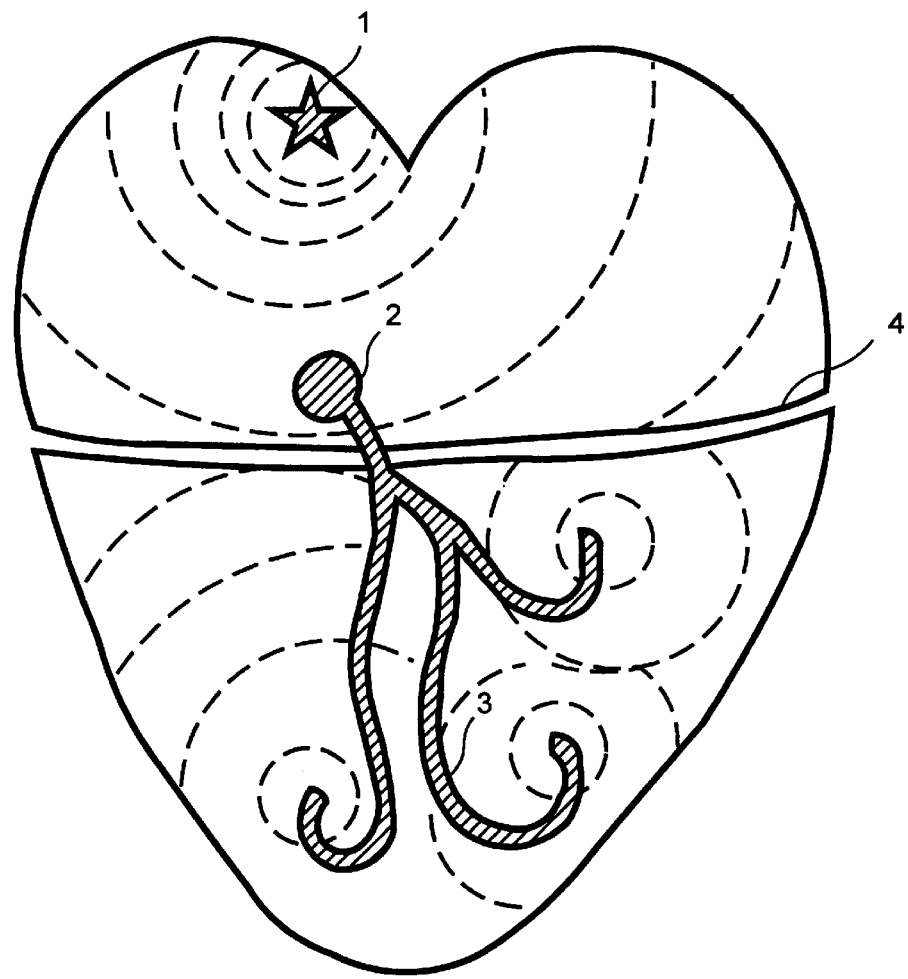
FIG. 2A is a schematic illustration of the conventional conduction system of the heart.

For the sake of easier understanding of the invention, the conduction system of the heart will now be briefly explained, with reference to FIG. 2. In the figure, the heart of a patient is shown from the front side, i.e. to the right hand in the figure is to the left on the patient, and vice versa. The rhythm of the heart is controlled from the sinoatrial node 1, sending out an electrical signal which is illustrated by approximately concentric, dashed circles. The signals reach the atrio-ventricular node (AV node) 2, acting as a collector and filter for the impulses from the sinoatrial node. The signals are transferred by a "wire harness" of cardiomuscular fibres 3, to the ventricles. The atria and the ventricles are otherwise electrically insulated by a barrier 4.

Figure 2B:
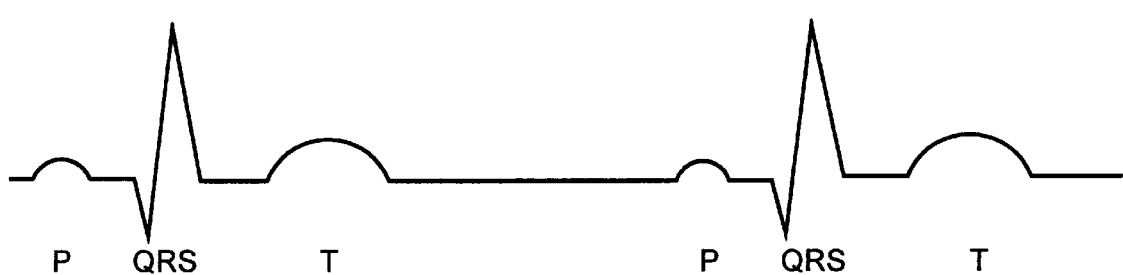
FIG. 2B shows a normal ECG curve.

FIG. 2B shows a normal ECG curve. The first pulse P originates from the sinoatrial node, whereas the QRS complex and the T wave emanate from the ventricles.

Figure 3A:
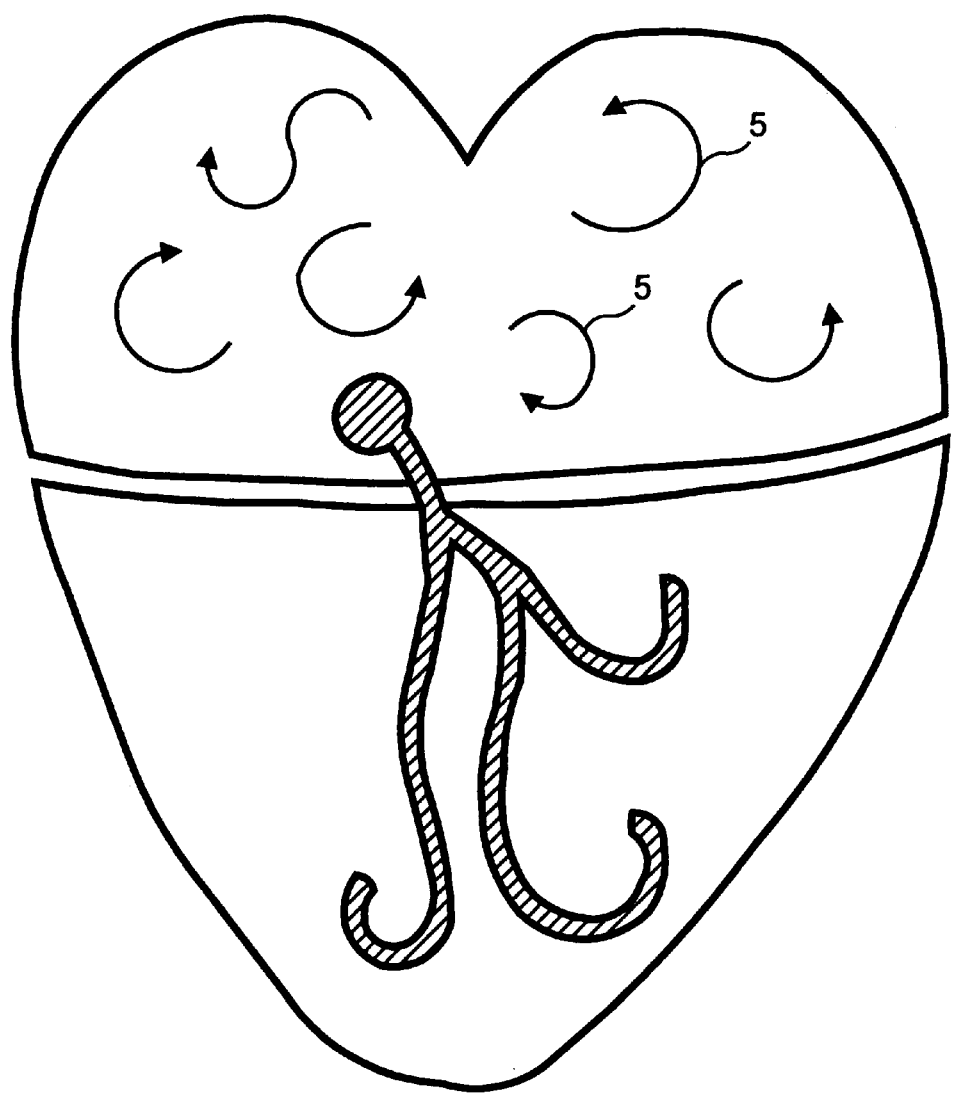
FIG. 3A is a schematic illustration of a heart exhibiting known atrial fibrillation.

FIG. 3A shows a heart with atrial fibrillation. From the figure it may be seen that the sinoatrial node cannot perform its function, because feedback loops 5 have in some way occurred in the atria and make a concentric propagation of the sinoatrial node impulses impossible. A feedback loop may occur around a functional or anatomical obstacle. A typical feature is the absence of the so called P wave in the ECG.

Figure 3B:
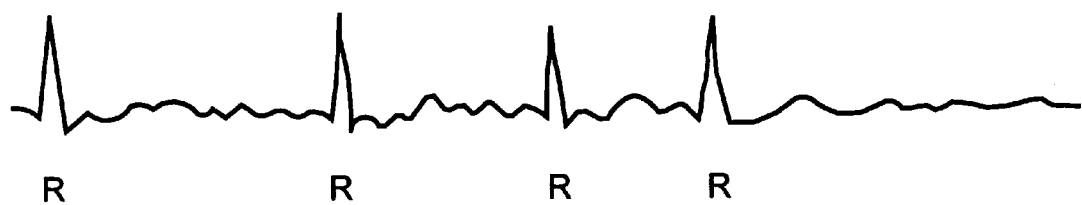
FIG. 3B is a curve illustrating a conventional electrical signal obtained in connection with known atrial fibrillation.

FIG. 3B shows a typical signal from a heart with atrial fibrillation. The signal consists of a fibrillation signal superimposed on the ventricular signal, of which the peaks R are easily identifiable.

The following applies:

$$WL \geq CV \times RP$$

where WL is the wave length ($\sim 1/f$), CV is the conduction velocity and RP is the refractory period, i.e. the recovery period of the cardiomuscular fibre after excitation by an electrical pulse. It has been found that the shorter the wave length, that is, the higher the frequency, the more difficult it is to treat a heart for fibrillation. Consequently, it is of interest to study the frequency of the atrial fibrillation, which the present inventor have realized.

Figure 4A:
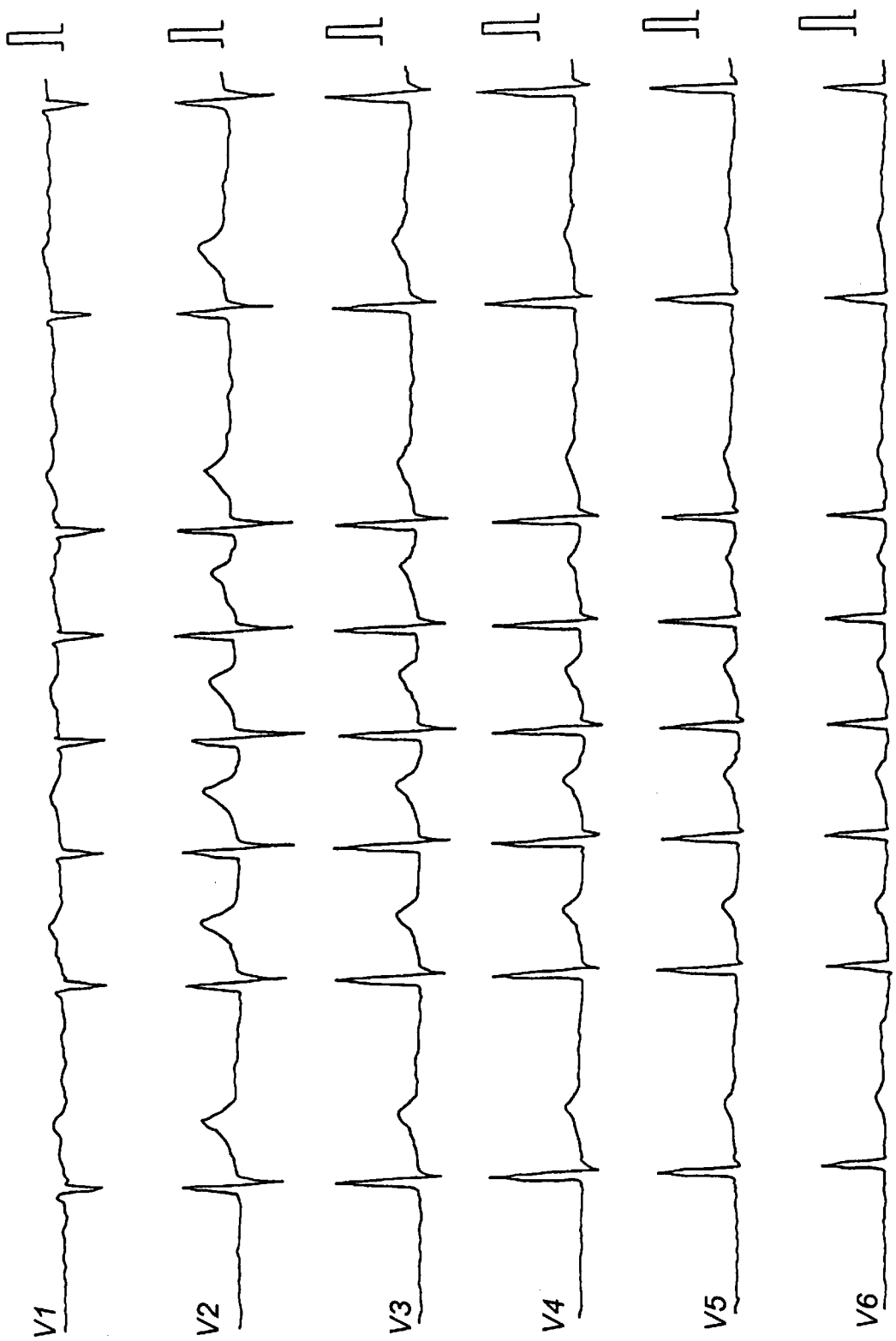
FIGS. 4A and 4B show various known curves from an ECG registration on a patient with atrial fibrillation.
Figure 4B:
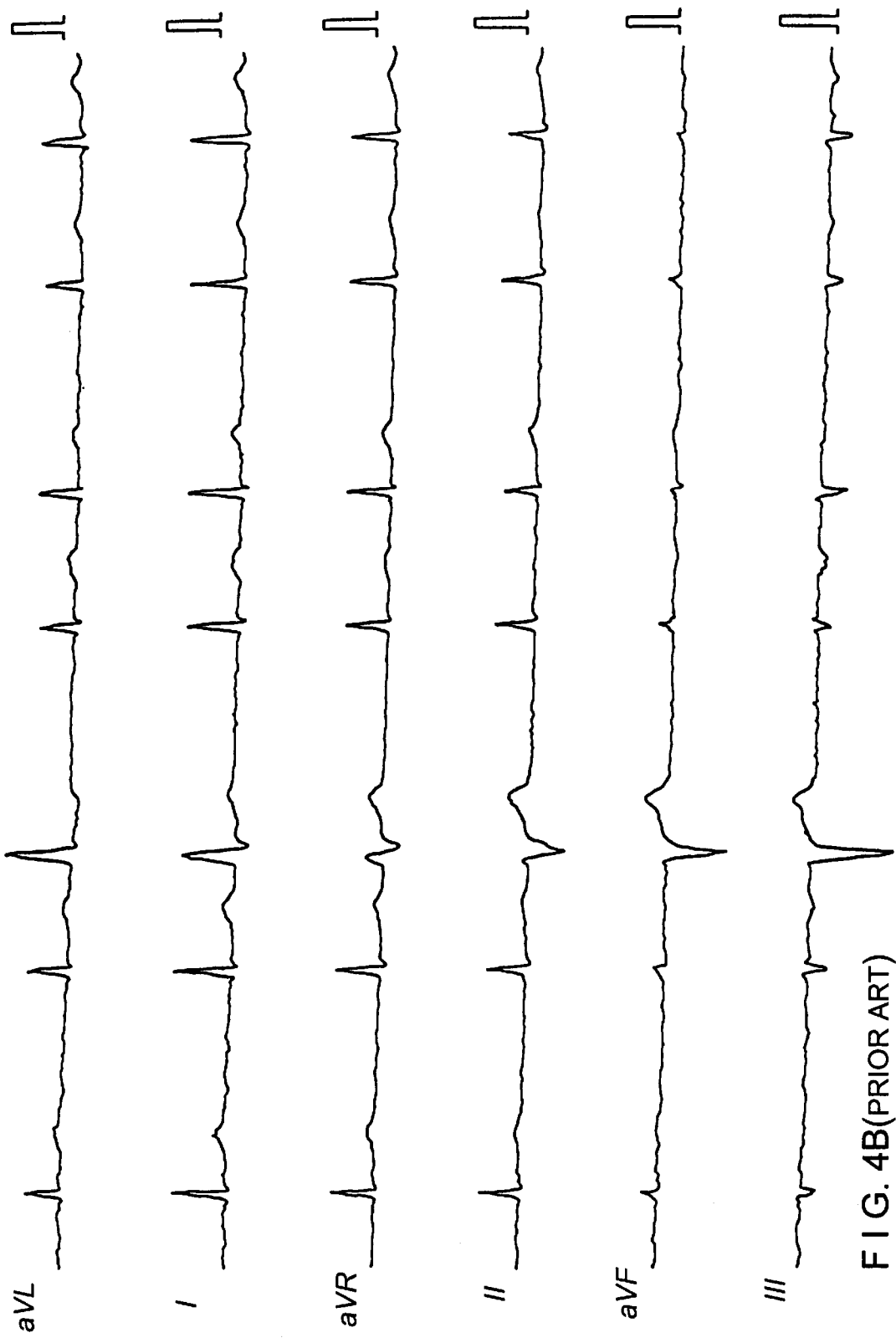

In FIGS. 4A and 4B, a registration is shown of an ECG on a patient with atrial fibrillation. The various signals V1–V6, AVL, I, -aVR, II, aVF, III are those normally registered during an ECG by surface electrodes applied to the body of the patient at conventional locations. If the heart had been healthy, a P wave could have been observed, which would have been most clearly visible in the signals V1 and II. Now, there is instead a superimposed fibrillation signal occurring.

Figure 5:
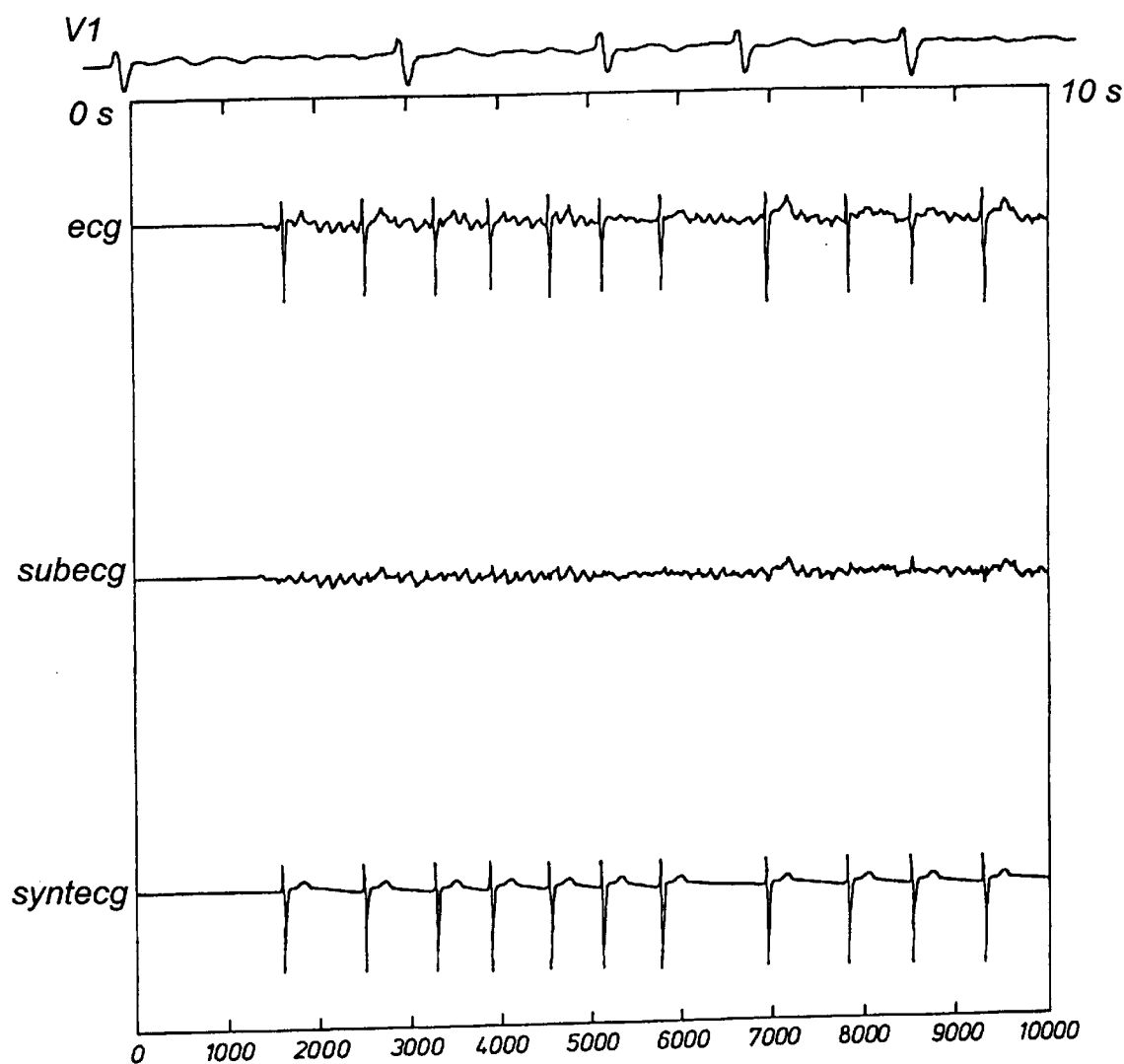
FIG. 5 is a diagram showing an ECG curve as well as a separated atrium curve and a separated ventricle curve.

In FIG. 5 is shown how, with the aid of the present invention, the fibrillation signal or atrial signal is extracted. The unprocessed ECG signal V1 is shown at the top of the figure. A conventional ECG equipment is supplemented with various devices for processing the ECG signal. First, the easily identifiable QRS peaks are identified. The QRS peaks are then individually classified into various types. Subsequently, a time average over the registration period is formed within each type. The averages of the classes are then subtracted from the total ECG signal, whereby the pure fibrillation signal subecg is obtained. The diagram also shows the signal syntecg which has been calculated and which is subtracted from the total signal. This signal corresponds to the "ventricular signal".

Figure 6:
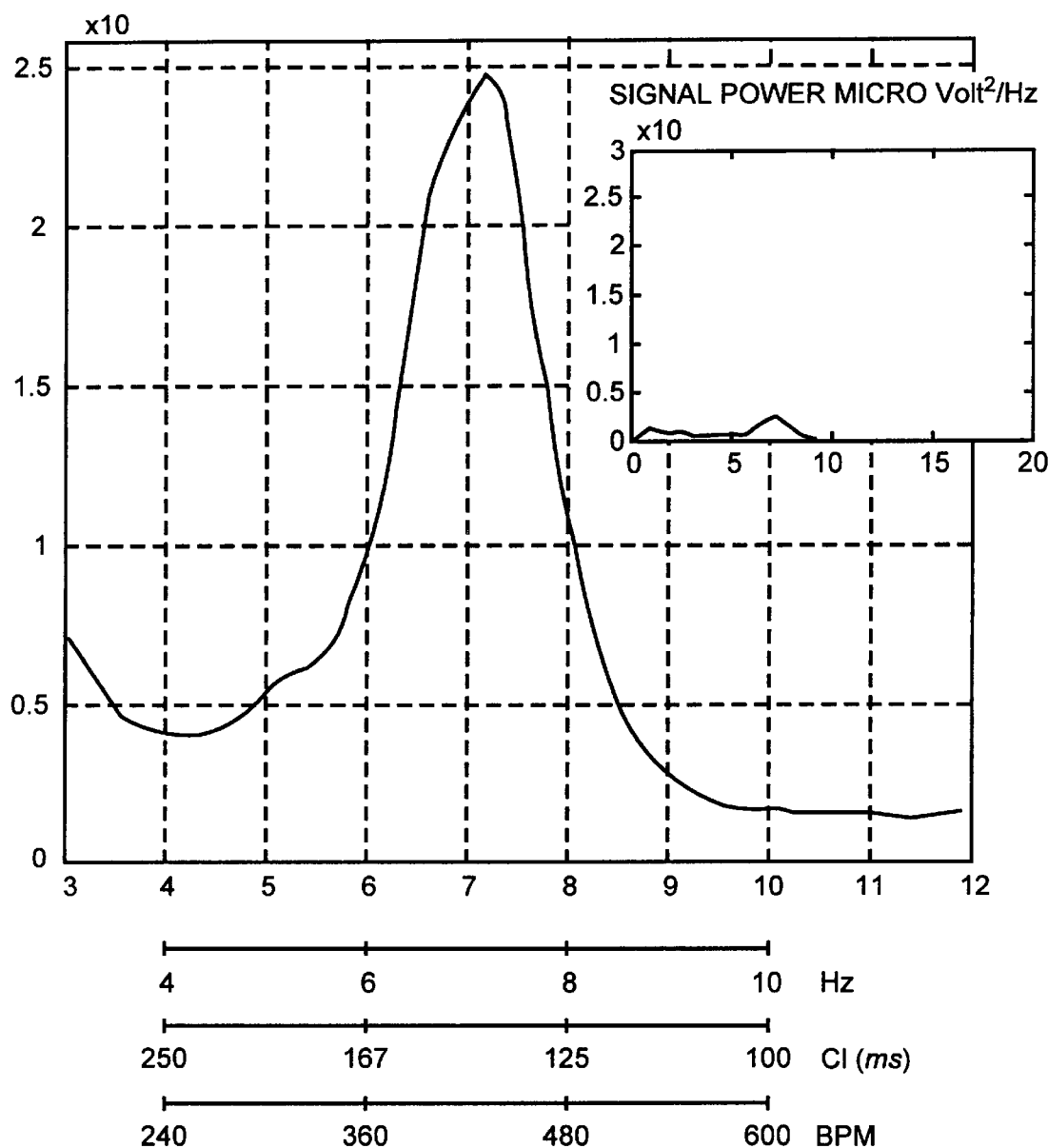
FIG. 6 is a diagram illustrating an example of frequency analysis of the atrium curve of FIG. 5.

The fibrillation signal obtained can be analysed subsequently with a frequency analyzer. FIG. 6 shows a diagram of such an analysis. As can be seen, the fibrillation has a frequency peak at about 7 Hz, which corresponds to a cycle length C1 of about 145 ms and 420 beats per minute (BPM). A lower value of the cycle length (or a higher frequency) for the location of the peak in the frequency analysis corresponds to a higher tendency towards arrhythmia. It may also be of interest to study the distribution of the pulse frequency, e.g. the pulse width at a given level.

This type of signal processing can also be performed on signals registered in the esophagus, or from the inside of the heart via cardiac catheters.

As a complement to the surface electrodes of the ECG equipment, oesophagal electrodes may be used. Such electrodes are swallowed by the patient, into the esophagus, and are positioned close to the heart. It is possible to come especially close to the atrium and the ventricle on the left side. With the aid of the esophagal electrodes, signals from a more delimited part of the heart may be selected. This may be of use during a study of the origin and the mechanism of the fibrillation.

The present invention thus provides a further development of the ECG technique for qualitative studies of especially atrial fibrillation. The major advantage over conventional ECG is that it enables an assessment of whether resources should be used, in the form of time, medicine and electrical treatment, or a patient with atrial fibrillation. The various means for registration of the electrical signals and for processing them, in the way prescribed by the invention, are based on conventional technology and do not present any design problems to a person skilled in the art. Machinery and software for frequency analysis and signal separation are commercially available. The scope of the invention is only limited by the accompanying claims.

What is claimed is:

1. Apparatus for frequency analysis of atrial fibrillation, characterized by a means for registration of electrical signals from the heart of a patient;

a means for separating a signal originating from the atria from the registered electrical signals; and a means for frequency analysis of the atrial signal.

2. Apparatus according to claim 1, characterized in that the separating means comprises devices for identification of signals originating from the ventricles, devices for classification of the ventricular signals, devices for formation of the average of the classified ventricular signals and devices for subtracting said averaged, classified ventricular signals from the total registered signal, in order to obtain the atrial signal.

3. Apparatus according to claim 1, characterized in that the registration means comprises surface electrodes to be placed on the patient.

4. Apparatus according to claim 3, characterized in that the registration means comprises surface electrodes for ECG registration.

5. Apparatus according to claim 3, characterized in that the registration means comprises electrodes for location inside the esophagus of the patient, for selective registration of signals.

6. Apparatus according to claim 2, characterized in that the registration means comprises electrodes for location inside the heart of the patient via cardiac catheters, for selective registration of signals.

7. Apparatus according to claim 1 or 2, characterized in that the frequency analysis means comprises devices for the calculation and display of the mean frequency of the atrial fibrillation and a distribution value.

* * * * *